United States Patent

Asiri

(10) Patent No.: US 8,258,300 B2
(45) Date of Patent: Sep. 4, 2012

(54) AZO DYES

(75) Inventor: Abdullah Mohamed Asiri, Jeddah (SA)

(73) Assignee: King Abdulaziz University, Jeddah (SA)

(*) Notice: Subject to any disclaimer, the term of this patent is extended or adjusted under 35 U.S.C. 154(b) by 881 days.

(21) Appl. No.: 12/285,127

(22) Filed: Sep. 29, 2008

(65) Prior Publication Data

US 2010/0081823 A1    Apr. 1, 2010

(51) Int. Cl.
C07D 221/22 (2006.01)
C07D 293/00 (2006.01)
A61K 31/4375 (2006.01)

(52) U.S. Cl. ............... 546/97; 548/1; 514/294; 514/296

(58) Field of Classification Search .................. 546/97; 514/294, 296

See application file for complete search history.

(56) References Cited

U.S. PATENT DOCUMENTS

| | | |
|---|---|---|
| 4,743,581 A | 5/1988 | Gregory et al. |
| 4,764,178 A | 8/1988 | Gregory et al. |
| 4,977,135 A | 12/1990 | Bradbury et al. |
| 5,070,069 A | 12/1991 | Bradbury et al. |
| 5,158,928 A | 10/1992 | Bach et al. |
| 5,194,463 A | 3/1993 | Krutak et al. |
| RE34,877 E | 3/1995 | Bach et al. |
| 6,197,223 B1 | 3/2001 | Weaver et al. |
| 6,776,930 B2 | 8/2004 | Weaver et al. |
| 2001/0023938 A1 | 9/2001 | Allen et al. |
| 2004/0195552 A1 | 10/2004 | Weaver et al. |

FOREIGN PATENT DOCUMENTS

DE    3817565    * 12/1988

* cited by examiner

*Primary Examiner* — Rita Desai
(74) *Attorney, Agent, or Firm* — Richard C. Litman

(57) ABSTRACT

The azo dyes relate to thiophene azo dyes of the general formula:

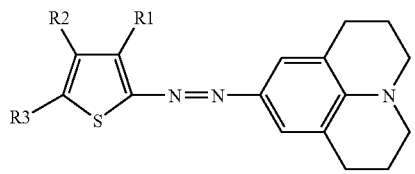

where R1 is Cyano or C1-C5 alkoxy carbonyl; R2 is hydrogen, halogene, C1-C2 alkyl, phenyl, or substituted phenyl; and R3 is C1-C5 alkoxy carbonyl, C1-C4 alkanoyl, benzoyl, phenyl, alkyl substituted phenyl, or alkoxy phenyl; or R2 and R3 are fused cycloalkane with C3-C5.

5 Claims, No Drawings

AZO DYES

BACKGROUND OF THE INVENTION

Field of the Invention

The present invention relates to azo dyes, and particularly to azo dyes formed from 2-aminothiophene with a julolidine coupling component.

SUMMARY OF THE INVENTION

The azo dyes relate to thiophene azo dyes of the general formula:

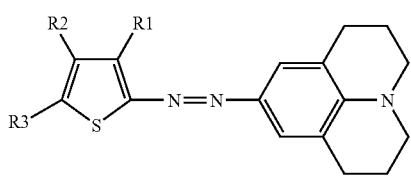

I where R1 is cyano or C1-C5 alkoxy carbonyl; R2 is hydrogen, halogene, C1-C2 alkyl, phenyl, or substituted phenyl; and R3 is C1-C5 alkoxy carbonyl, C1-C4 alkanoyl, benzoyl, phenyl, alkyl substituted phenyl, or alkoxy phenyl; or R2 and R3 are fused cycloalkane with C3-C5.

In these compounds, the coupling component is julolidine, having formula II, and the diazo component is 2-aminothiophene (formula III) substituted at the 3, 4, and/or 5 positions.

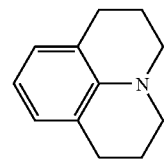

II

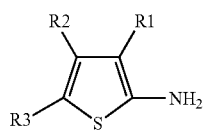

III

Azo dyes of the general formula I may be used to color polyesters, polyethylene, and other thermoplastic polymers. The dyes have high molar absorptions and produce a deep hue of color on polyester.

These and other features of the present invention will become readily apparent upon further review of the following specification and drawings.

BRIEF DESCRIPTION OF THE DRAWINGS

The sole drawing is the ultraviolet-visible spectra of dye 1 in various solvents.

Similar reference characters denote corresponding features consistently throughout the attached drawings.

DETAILED DESCRIPTION OF THE PREFERRED EMBODIMENTS

The azo dyes relate to thiophene azo dyes of the general formula:

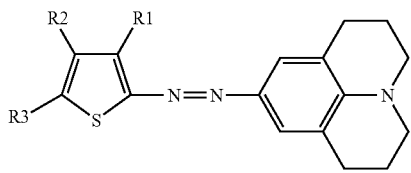

I where R1 is cyano or C1-C5 alkoxy carbonyl; R2 is hydrogen, halogene, C1-C2 alkyl, phenyl, or substituted phenyl; and R3 is C1-C5 alkoxy carbonyl, C1-C4 alkanoyl, benzoyl, phenyl, alkyl substituted phenyl, or alkoxy phenyl; or R2 and R3 are fused cycloalkane with C3-C5.

In these compounds, the coupling component is julolidine, having formula II, and the diazo component is 2-aminothiophene (formula III) substituted at the 3, 4, and/or 5 positions. The 2-aminothiophene may be prepared using a Gewald reaction (condensation of an α-ketone or aldehyde with an α-cyanoester in the presence of elemental sulfur and base).

The azo dyes may have any of the following thirteen configurations.

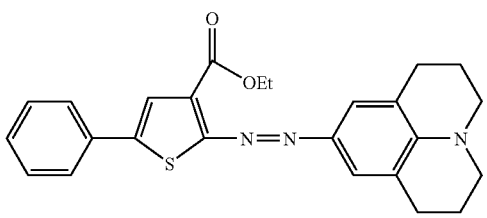

1

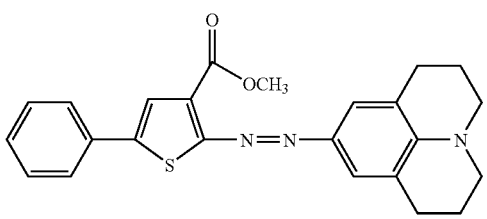

2

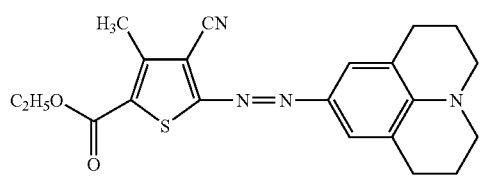

3

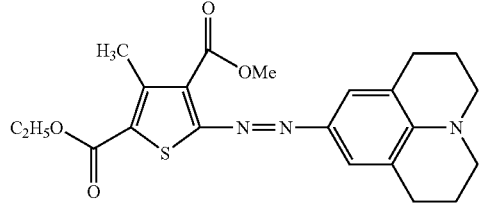

4

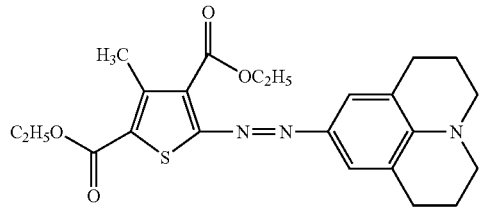

5

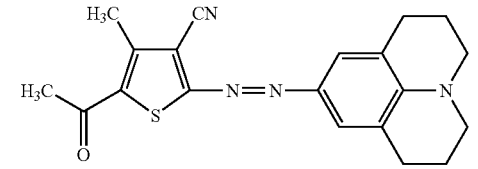

6

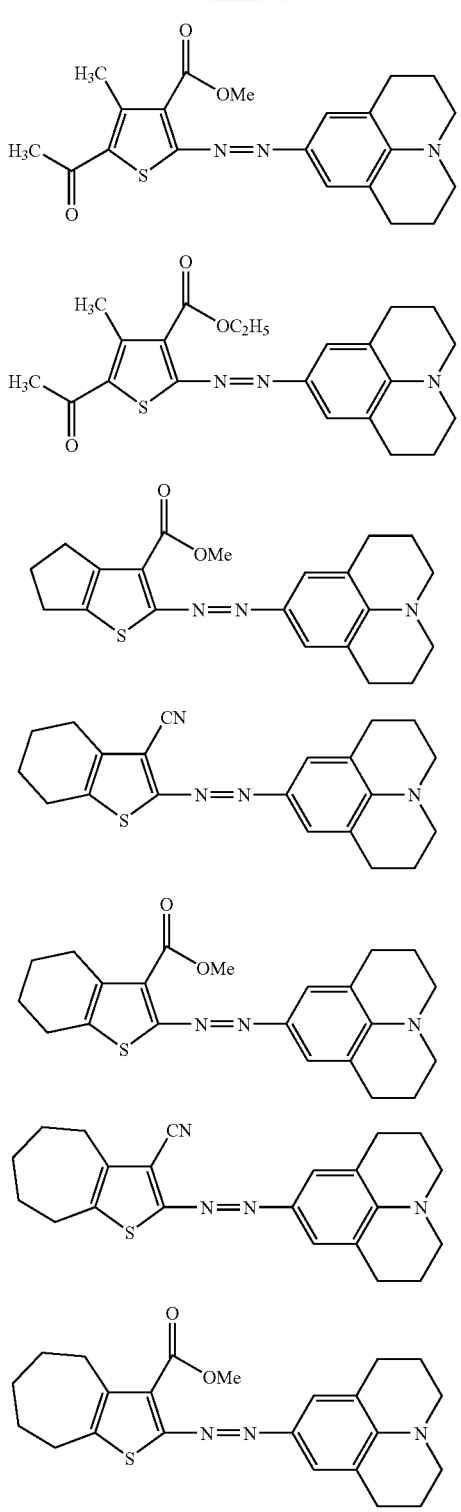

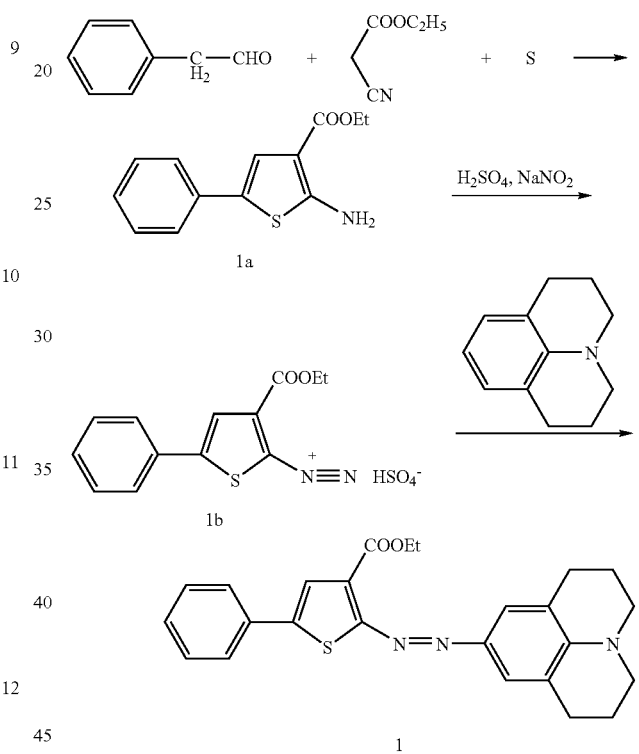

Exemplary methods of preparing the aminothiophene azo dyes are illustrated in the following examples.

Example 1

The reaction scheme for the synthesis of azo dye 1 is shown below. In a Gewald reaction, diethylamine (8 ml) was added to a solution of equimolar quantities of phenylacetaldehyde (12.0 g, 0.10 mol) and ethylcyanoacetate (11.4 g, 0.10 mol) in ethanol and was refluxed for 10 minutes then sulfur (3.53 g, 0.11 mol) was added, and the solution was refluxed for further 3 hours. The pale yellow precipitate formed was filtered and washed with cooled ethanol to give 1a as pale yellow powder (4.70 g, 19% yield), mp. 124-125° C.

The substituted 2-aminothiophene 1a (1.5 gm, 6.0 mmol) was dissolved in minimum amounts of dimethylformamide (5 ml), and sulfuric acid (4 ml, 54% V/V) was added. The dissolved solid was cooled to 0-5° C. with stirring for half an hour. Sodium nitrite (0.5 g, 6.0 mmol) was dissolved in water (5 ml) and cooled to 0-5° C. to form dilute nitrous acid. This solution was slowly added to the 2-aminothiophene derivative solution with the temperature kept in the range of 0-5° C. Stirring was continued for one hour, after which the diazonium salt 1b was formed.

Julolidine (1.04 g, 6.0 mmol) was dissolved in a solution prepared from water (10 ml) and hydrochloric acid (2 ml, 10M), and the solution was cooled to a temperature between 0-5° C. The diazonium solution 1b was added to the Julolidine coupling component solution slowly over a period of one hour to keep the temperature below 5° C. Stirring was continued for 2 hours, during which the temperature was raised to room temperature. The pH of the solution was raised by adding sodium hydroxide solution (5-10%) to maintain the pH in the range between 5.5 and 7. The precipitated dye 1 was then filtered and washed with plenty of water to get rid of the excess sodium hydroxide, and then recrystallized from ethyl acetate/petroleum ether (40-60) mixture (8:2). m.p. 183-186, (81% yield).

The ultraviolet-visible spectra of azo dye 1 in various solvents are shown in FIG. 1.

Example 2

The reaction scheme for the synthesis of azo dye 2 is shown below. In a Gewald reaction, diethylamine (8 ml) was added to a solution of equimolar quantities of phenylacetaldehyde (12.0 g, 0.10 mol) and methylcyanoacetate (9.90 g, 0.10 mol) in ethanol. The mixture was refluxed for 10 minutes, then sulfur (3.53 g, 0.11 mol) was added, and the solution was refluxed for further three hours. The pale yellow precipitate formed was filtered and washed with cooled ethanol to give 2a as pale yellow powder (5.83 g, 25% yield), mp. 196-197° C.

to a solution of equimolar quantities of ethyl acetoacetate (13.0 g, 0.10 mol) and malononitrile (6.60 g, 0.10 mol) in ethanol and was refluxed for 10 minutes, then sulfur (3.53 g, 0.11.0 mol) was added, and the solution was refluxed for a further three hours. The pale yellow precipitate formed was filtered and washed with cooled ethanol to give 3a as pale yellow powder (10.1 g, 54% yield), mp 298-296° C.

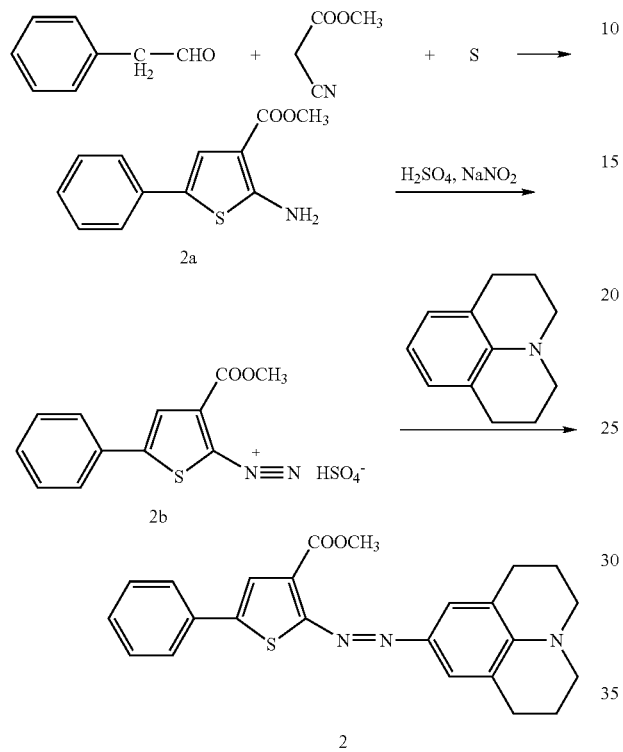

2

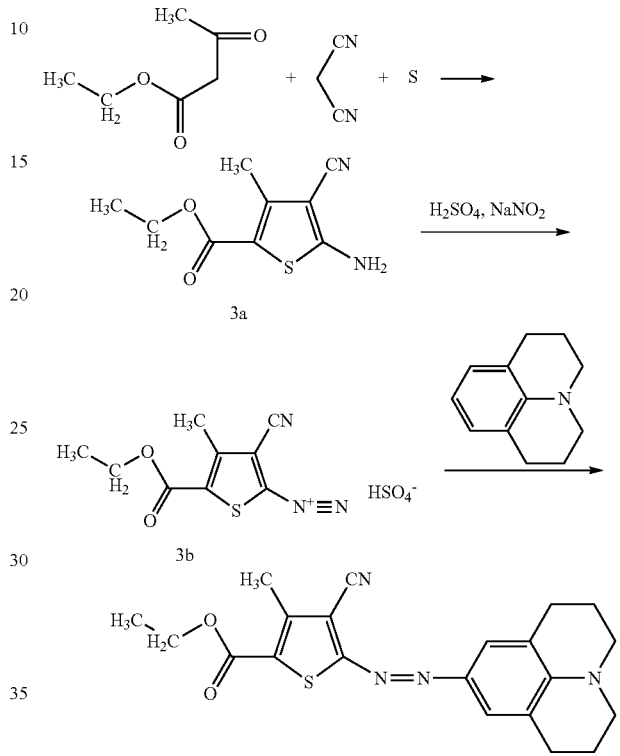

3

The substituted 2-aminothiophene 2a (2.5 g, 10.7 mmol) was dissolved in minimum amounts of dimethylformamide (5 ml), and sulfuric acid (6 ml, 54% V/V) was added. The dissolved solid was cooled to 0-5° C. with stirring for half an hour. Sodium nitrite (0.74 g, 10.7 mmol) dissolved in water (10 ml) and cooled to 0-5° C. to form dilute nitrous acid. This solution was slowly added to the 2-aminothiophene derivative solution with the temperature being kept in the range of 0-5° C., and stirring was continued for one hour, after which the diazonium salt 2b was formed.

Julolidine (1.85 g, 10.7 mmol) was dissolved in a solution prepared from water (10 ml) and hydrochloric acid (3 ml, 10M), and the solution was cooled to a temperature between 0-5° C. The diazonium solution 2b was added to the Julolidine coupling component solution slowly over a period of one hour to keep the temperature below 5° C. Stirring was continued for 2 hours, during which the temperature was raised to room temperature. The pH of the solution was raised by adding sodium hydroxide solution (5-10%) to obtain a pH in the range between 5.5 and 7. The precipitated dye 2 was filtered and washed with plenty of water to get rid of the excess sodium hydroxide, then recrystallized from ethyl acetate/petroleum ether (40-60) mixture (8:2), m.p. 194-197, (79% yield).

Example 3

The reaction scheme for the synthesis of azo dye 3 is shown below. In a Gewald reaction, diethylamine (8 ml) was added The substituted 2-aminothiophene 3a (5.36 gm, 0.0256 mol) was dissolved in minimum amounts of dimethylformamide (10 ml), and sulfuric acid (8 ml, 54% V/V) was added. The dissolved solid was cooled to 0-5° C. with stirring for half an hour. Sodium nitrite (1.76 g, 0.0256 mmol) was dissolved in water (10 ml) and cooled to 0-5° C. to form dilute nitrous acid. This solution was slowly added to the 2-aminothiophene derivative solution with the temperature being kept in the range of 0-5° C. Stirring was continued for one hour, after which the diazonium salt 3b was formed.

Julolidine (4.42 g, 0.0255 mmol) was dissolved in a solution prepared from water (10 ml) and hydrochloric acid (5 ml, 10M), and the solution was cooled to a temperature between 0-5° C. The diazonium solution 3b was added to the Julolidine coupling component solution slowly over a period of one hour to keep the temperature below 5° C. Stirring was continued for two hours, during which the temperature was raised to room temperature. The pH of the solution was raised by adding sodium hydroxide solution (5-10%) to obtain a pH in the range between 5.5-7. The precipitated dye 3 was filtered and washed with plenty of water to get rid of the excess sodium hydroxide, then recrystallized from ethyl acetate/petroleum ether (40-60) mixture (8:2), m.p. 196-198° C., (80% yield).

Example 4

The reaction scheme for the synthesis of azo dye 4 is shown below. In a Gewald reaction, diethylamine (8 ml) was added to a solution of equimolar quantities of ethyl acetoacetate (13.0 g, 0.10 mol) and methylcyanoacetate (9.90 g, 0.10 mol) in ethanol, and the mixture was refluxed for 10 minutes. Then sulfur (3.53 g, 0.11 mol) was added, and the solution was refluxed for a further 3 hours. The pale yellow precipitate that formed was filtered and washed with cooled ethanol to give 4a as a pale yellow powder (10.2 g, 52% yield), m.p. 95-97° C.

to a solution of equimolar quantities of ethyl acetoacetate (13.0 g, 0.10 mol) and ethylcyanoacetate (11.3 g, 0.10 mol) in ethanol, and the mixture was refluxed for 10 minutes. Then sulfur (3.53 g, 11.0 mmol) was added, and the solution was refluxed for a further 3 hours. The pale yellow precipitate that formed was filtered and washed with cooled ethanol to give 5a as pale yellow powder (9.26 g, 50% yield), m.p. 107-109° C.

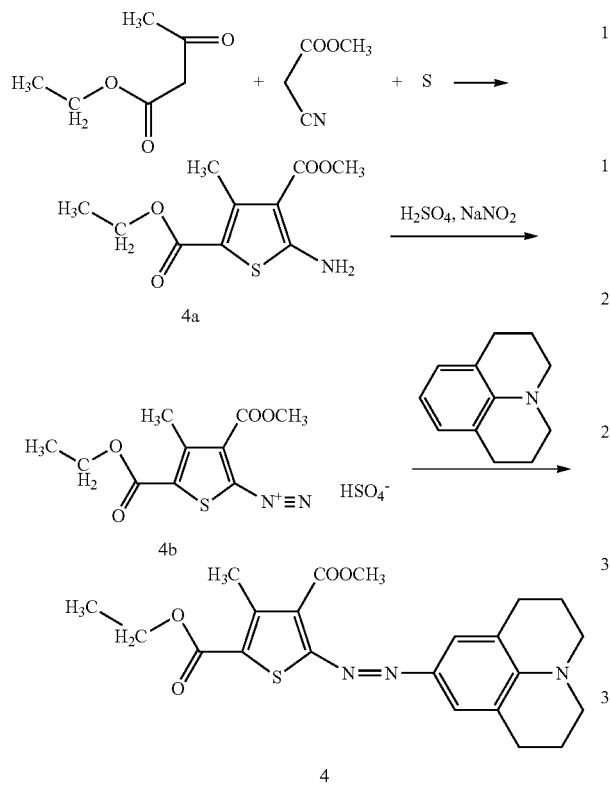

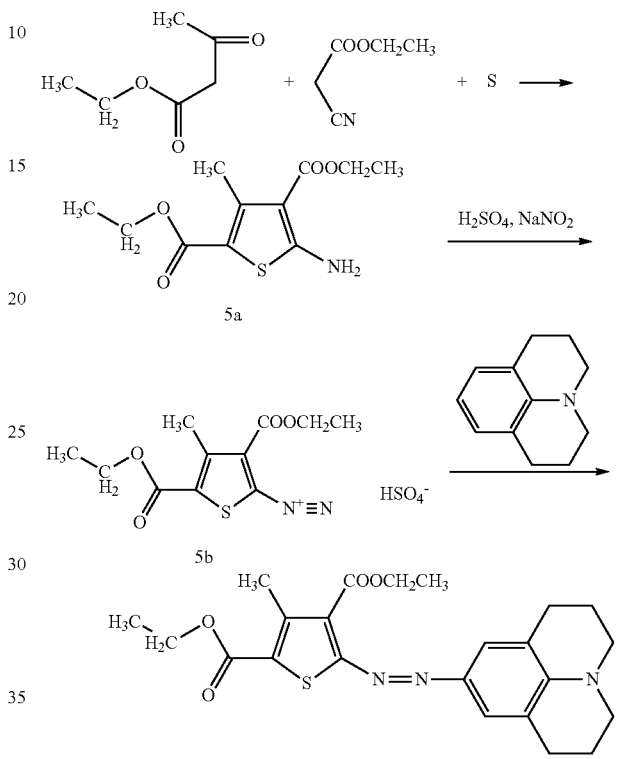

The 2-aminothiophene derivative 4a (4.94 gm, 0.0203 mol) was dissolved in minimum amounts of dimethylformamide (10 ml), and sulfuric acid (8 ml, 54% V/V) was added. The dissolved solid was cooled to 0-5° C. with stirring for half an hour. Sodium nitrite (1.40 g, 0.0203 mol) was dissolved in water (10 ml) and cooled to 0-5° C. to form dilute nitrous acid. This solution was slowly added to the 2-aminothiophene derivative solution, with the temperature being kept in the range of 0-5° C. Stirring was continued for one hour, after which the diazonium salt 4b was formed.

Julolidine (3.52 g, 0.0203 mmol) was dissolved in a solution prepared from water (10 ml) and hydrochloric acid (5 ml, 10M), and the solution was cooled to a the temperature between 0-5° C. The diazonium solution 4b was added to the julolidine coupling component solution slowly over a period of one hour to keep the temperature below 5° C. The reaction mixture was stirred for 2 hours, during which the temperature was raised to room temperature. The pH of the solution was raised by adding sodium hydroxide solution (5-10%) to obtain a pH in the range between 5.5-7. The precipitated dye 4 was filtered and washed with plenty of water to get rid of the excess sodium hydroxide, then recrystallized from ethyl acetate/petroleum ether (40-60) mixture (8:2) m.p. 127-129° C., (30% yield).

Example 5

The reaction scheme for the synthesis of azo dye 5 is shown below. In a Gewald reaction, diethylamine (8 ml) was added The 2-aminothiophene derivative 5a (5.56 gm, 0.0216 mmol) was dissolved in minimum amounts of dimethylformamide (10 ml), and sulfuric acid (8 ml, 54% V/V) was added. The dissolved solid was cooled to 0-5° C. with stirring for half an hour. Sodium nitrite (1.49 g, 0.0216 mmol), dissolved in water (10 ml), was added, and the mixture was cooled to 0-5° C. This solution was slowly added slowly to the 2-aminothiophene derivative solution with temperature being kept in the range of 0-5° C. Stirring was continued for one hour, after which the diazonium salt 5b was formed.

Julolidine (3.74 g, 0.0216 mmol) was dissolved in a solution prepared from water (10 ml) and hydrochloric acid (5 ml, 10M), and the solution was cooled to a temperature between 0-5° C. The diazonium solution 5b was added to the Julolidine coupling component solution slowly over a period of one hour to keep the temperature below 5° C. The reaction mixture was stirred for 2 hours, during which the temperature was raised to room temperature. The pH of the solution was raised by adding sodium hydroxide solution (5-10%) to obtain a pH in the range between 5.5 and 7. The precipitated dye 5 was filtered and washed with plenty of water to get rid of the excess sodium hydroxide, then recrystallized from an ethyl acetate/petroleum ether (40-60) mixture (8:2), m.p. 117-119° C., (33% yield).

Example 6

The reaction scheme for the synthesis of azo dye 6 is shown below. In a Gewald reaction, diethylamine (8 ml) was added to a solution of equimolar quantities of acetylacetone (10.0 g, 0.10 mol) and malononitrile (6.60 g, 0.10 mol) in ethanol, and the mixture was refluxed for 10 minutes. Then sulfur (3.53 g, 0.11 mol) was added, and the solution was refluxed for a further 3 hours. The pale yellow precipitate the formed was filtered and washed with cooled ethanol to give 6a as pale yellow powder (8.58 g, 51% yield), m.p. 295-296° C.

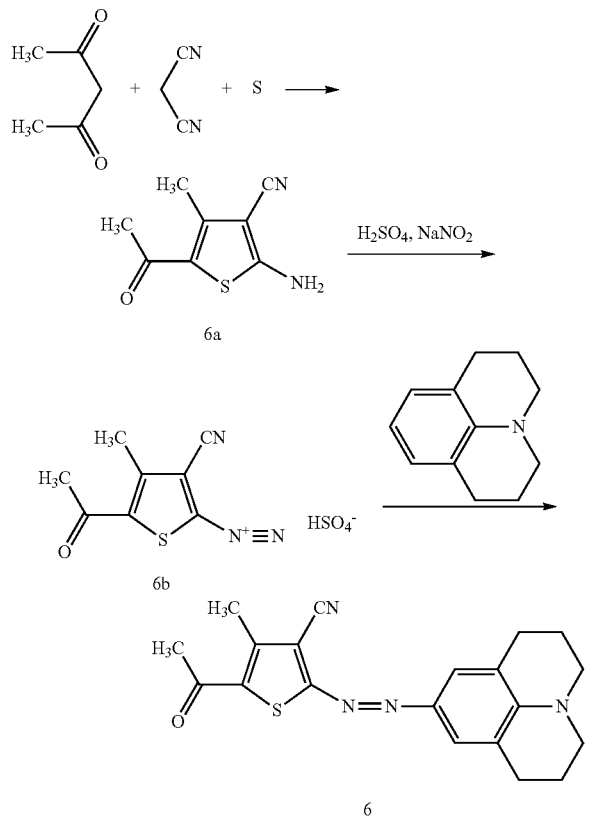

The 2-aminothiophene derivative 6a (5.42 g, 0.0301 mmol) was dissolved in minimum amounts of dimethylformamide (10 ml), and sulfuric acid (8 ml, 54% V/V) was added. The mixture was cooled to 0-5° C. with stirring for half an hour. Sodium nitrite (2.08 g, 0.0301 mmol) was dissolved in water (10 ml) and cooled to 0-5° C. to form dilute nitrous acid. This solution was slowly added to the 2-aminothiophene derivative solution, with the temperature being kept in the range of 0-5° C. Stirring was continued for one hour, after which the diazonium salt 6b was formed.

Julolidine (5.22 g, 0.0301 mmol) was dissolved in a solution prepared from water (10 ml) and hydrochloric acid (5 ml, 10 M), and the solution was cooled to the temperature between 0-5° C. The diazonium solution 6b was added to the julolidine coupling component solution slowly over a period of one hour to keep the temperature below 5° C. The reaction mixture was stirred for 2 hours, during which the temperature was raised to room temperature. The pH of the solution was raised by adding sodium hydroxide solution (5-10%) to obtain a pH in the range between 5.5 and 7. The precipitated dye 6 was filtered and washed with plenty of water to get rid of the excess sodium hydroxide, then recrystallized from an ethyl acetate/petroleum ether (40-60) mixture (8:2), m.p. 175-177° C. (72% yield).

Example 7

The reaction scheme for the synthesis of azo dye 7 is shown below. In a Gewald reaction, diethylamine (8 ml) was added to a solution of equimolar quantities of acetyl acetone (10.0 g, 0.10 mol) and methyl cyanoacetate (9.90 g, 0.10 mol) in ethanol. The mixture was refluxed for 10 minutes, then sulfur (3.53 g, 0.11 mol) was added, and the solution was refluxed for a further 3 hours. The pale yellow precipitate that formed was filtered and washed with cooled ethanol to give 7a as pale yellow powder (6.50 g, 33% yield), m.p. 164-166° C.

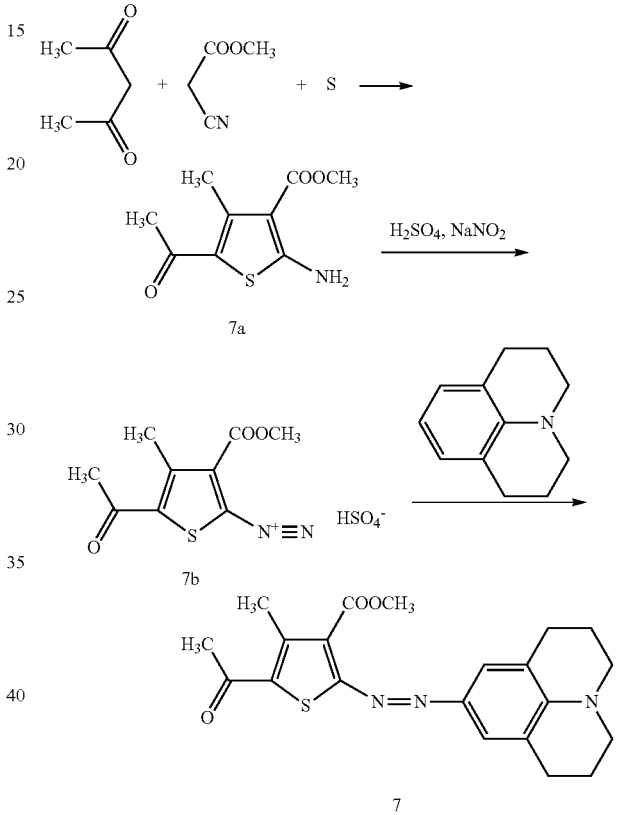

The 2-aminothiophene derivative 7a (5.40 g, 0.0253 mmol) was dissolved in minimum amounts of dimethylformamide (10 ml), and sulfuric acid (8 ml, 54% V/V) was added. The mixture was cooled to 0-5° C. with stirring for half an hour. Sodium nitrite (1.75 g, 0.0253 mmol) was dissolved in water (10 ml) and cooled to 0-5° C. to form dilute nitrous acid. This solution was slowly added to the 2-aminothiophene derivative solution with the temperature being kept in the range of 0-5° C. Stirring was continued for one hour, after which the diazonium salt 7b was formed.

Julolidine (4.38 g, 0.0253 mol) was dissolved in a solution prepared from water (10 ml) and hydrochloric acid (5 ml, 10M), and the solution was cooled to a temperature between 0-5° C. The diazonium solution 7b was added to the Julolidine coupling component solution slowly over a period of one hour to keep the temperature below 5° C. The reaction mixture was stirred for 2 hours, during which the temperature was raised to room temperature. The pH of the solution was raised by adding sodium hydroxide solution (5-10%) to obtain a pH in the range between 5.5 and 7. The precipitated dye 7 was filtered and washed with plenty of water to get rid of the excess sodium hydroxide, then recrystallized from an ethyl acetate/petroleum ether (40-60) mixture (8:2), m.p. 111-113° C., (49% yield).

Example 8

The reaction scheme for the synthesis of azo dye 8 is shown below. In a Gewald reaction, diethylamine (8 ml) was added to a solution of equimolar quantities of acetyl acetone (10.0 g, 0.10 mol) and ethyl acetoacetate (11.3 g, 0.10 mol) in ethanol. The mixture was refluxed for 10 minutes, then sulfur (3.53 g, 0.11 mol) was added. The solution was refluxed for a further 3 hours. The pale yellow precipitate that formed was filtered and washed with cooled ethanol to give 8a as pale yellow powder (11.0 g, 52% yield), m.p. 162-164° C.

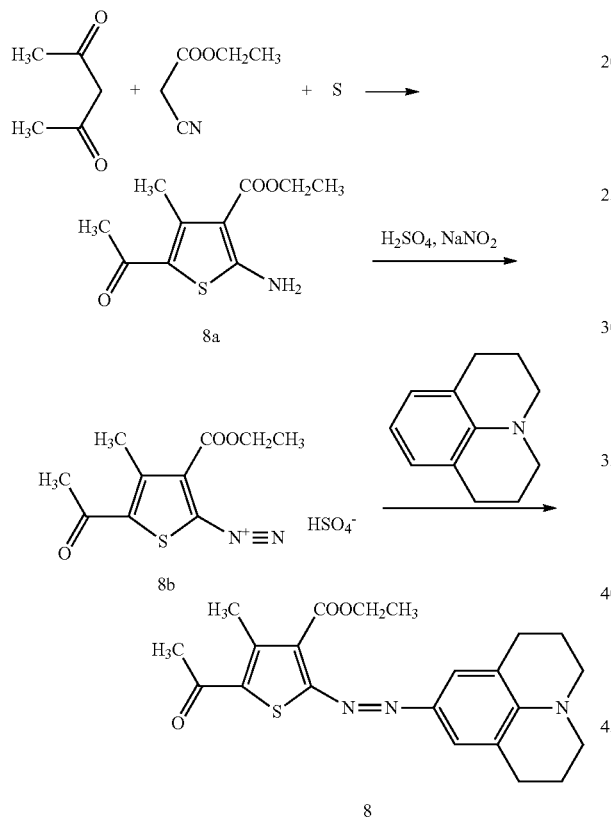

The 2-aminothiophene derivative 8a (5.45 g, 0.024 mol) was dissolved in a minimum amount of dimethylformamide (10 ml), and sulfuric acid (8 ml, 54% V/V) was added. The mixture was cooled to 0-5° C. with stirring for half an hour. Sodium nitrite (1.66 g, 0.024 mol) was dissolved in water (10 ml) and cooled to 0-5° C. to form dilute nitrous acid. This solution was slowly added to the 2-aminothiophene derivative solution, with the temperature being kept in the range of 0-5° C. Stirring was continued for one hour, after which the diazonium salt 8b was formed.

Julolidine (4.16 g, 0.024 mol) was dissolved in a solution prepared from water (10 ml) and hydrochloric acid (5 ml, 10M), and the solution was cooled to a temperature between 0-5° C. The diazonium solution 8b was added to the julolidine coupling component solution slowly over a period of one hour to keep the temperature below 5° C. The reaction mixture was stirred for 2 hours, during which the temperature was raised to room temperature. The pH of the solution was raised by adding sodium hydroxide solution (5-10%) to obtain a pH in the range between 5.5 and 7. The precipitated dye 8 was filtered and washed with plenty of water to get rid of the excess sodium hydroxide, then recrystallized from ethyl acetate/petroleum ether (40-60) mixture (8:2), m.p. 125-127° C., (21% yield).

Example 9

The reaction scheme for the synthesis of azo dye 9 is shown below. In a Gewald reaction, diethylamine (8 ml) was added to a solution of equimolar quantities of cyclopentanone (8.40 g, 0.10 mol) and methyl cyanoacetate (9.90 g, 0.10 mol) in ethanol. The mixture was refluxed for 10 minutes, and then sulfur (3.53 g, 0.11 mol) was added. The solution was refluxed for a further 3 hours. The pale yellow precipitate that formed was filtered and washed with cooled ethanol to give 9a as a pale yellow powder (12.8 g, 62% yield), m.p. 185-186° C.

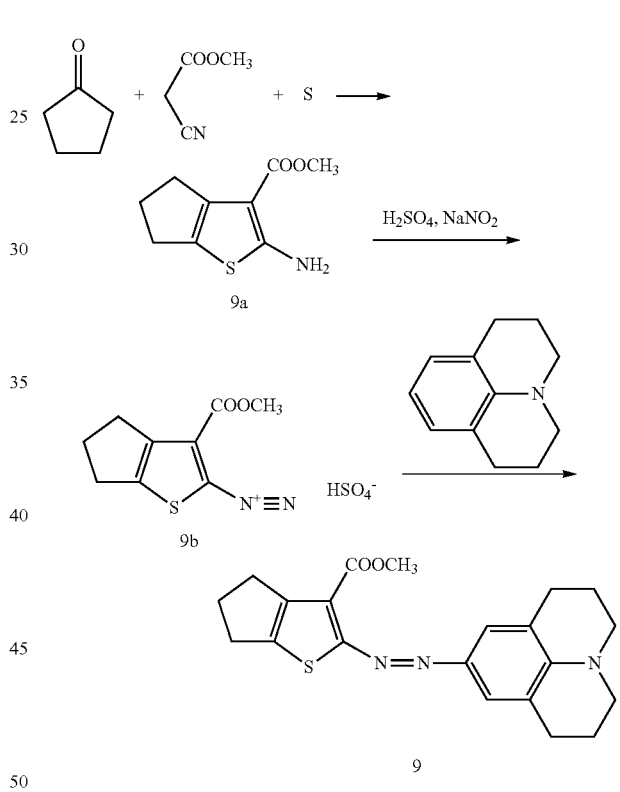

The 2-aminothiophene derivative 9a (5.0 g, 0.025 mol) was dissolved in a minimum amount of dimethylformamide (10 ml), and sulfuric acid (8 ml, 54% V/V) was added. The mixture was cooled to 0-5° C. with stirring for half an hour. Sodium nitrite (1.73 g, 0.025 mol) was dissolved in water (10 ml) and cooled to 0-5° C. to form dilute nitrous acid. This solution was slowly added to the 2-aminothiophene derivative solution, with the temperature being kept in the range of 0-5° C. Stirring was continued for one hour, after which the diazonium salt 9b was formed.

Julolidine (4.33 g, 0.025 mol) was dissolved in a solution prepared from water (10 ml) and hydrochloric acid (5 ml, 10M), and the solution was cooled to a temperature between 0-5° C. The diazonium solution 9a was added to the julolidine coupling component solution slowly over a period of one hour to keep the temperature below 5° C. The reaction mixture was stirred for 2 hours, during which the temperature was raised to room temperature. The pH of the solution was raised by adding sodium hydroxide solution (5-10%) to obtain a pH in the range between 5.5 and 7. The precipitated dye 9 was filtered and washed with plenty of water to get rid of the excess sodium hydroxide, then recrystallized from ethyl acetate/petroleum ether (40-60) mixture (8:2), m.p. 176-179° C., (67% yield).

Example 10

The reaction scheme for the synthesis of azo dye 10 is shown below. In a Gewald reaction, diethylamine (8 ml) was added to a solution of equimolar quantities of cyclohexanone (9.80 g, 0.10 mol) and malononitrile (6.60 g, 0.10 mol) in ethanol, and the mixture was refluxed for 10 minutes. Then sulfur (3.53 g, 0.11 mol) was added, and the solution was refluxed for a further 3 hours. The pale yellow precipitate that formed was filtered and washed with cooled ethanol to give 10a as a pale yellow powder (13.4 g, 75% yield), m.p. 147-148° C.

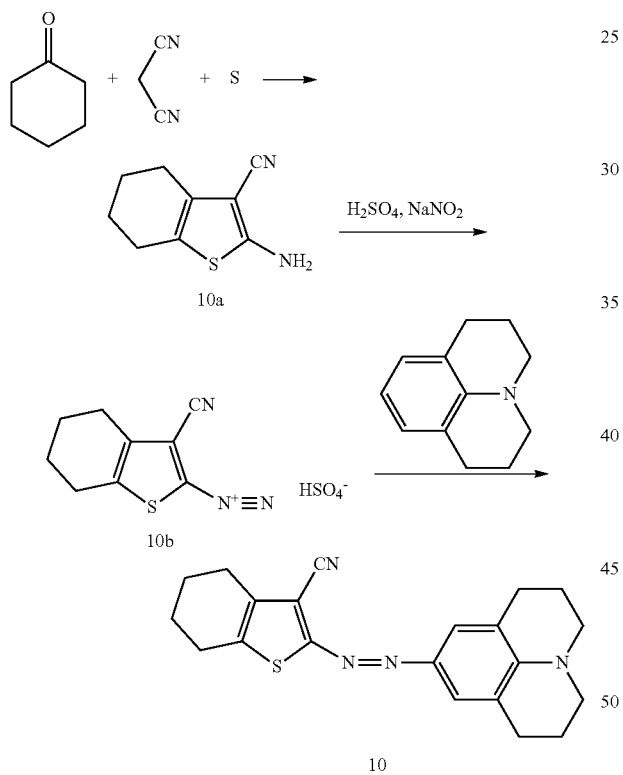

The 2-aminothiophene derivative 10a (5.0 g, 0.028 mol) was dissolved in a minimum amount of dimethylformamide (10 ml), and sulfuric acid (8 ml, 54% V/V) was added. The mixture was cooled to 0-5° C. with stirring for half an hour. Sodium nitrite (1.93 g, 0.028 mol) was dissolved in water (10 ml) and cooled to 0-5° C. to form dilute nitrous acid. This solution was slowly added to the 2-aminothiophene derivative solution, with the temperature being kept in the range of 0-5° C. Stirring was continued for one hour, after which the diazonium salt 10b was formed.

Julolidine (4.85 g, 0.028 mol) was dissolved in a solution prepared from water (10 ml) and hydrochloric acid (5 ml, 10 M), and the solution was cooled to a temperature between 0-5° C. The diazonium solution 10b was added to the Julolidine coupling component solution slowly over a period of one hour to keep the temperature below 5° C. The reaction mixture was stirred for 2 hours, during which the temperature was raised to room temperature. The pH of the solution was raised by adding sodium hydroxide solution (5-10%) to obtain a pH in the range between 5.5 and 7. The precipitated dye 10 was filtered and washed with plenty of water to get rid of the excess sodium hydroxide, then recrystallized from an ethyl acetate/petroleum ether (40-60) mixture (8:2), m.p. 116-122° C., (50% yield).

Example 11

The reaction scheme for the synthesis of azo dye 11 is shown below. In a Gewald reaction, diethylamine (8 ml) was added to a solution of equimolar quantities of cyclohexanone (9.80 g, 0.10 mol) and methyl cyanoacetate (9.90 g, 0.10 mol) in ethanol, and the mixture was refluxed for 10 minutes. Then sulfur (3.53 g, 0.11 mol) was added, and the solution was refluxed for a further 3 hours. The pale yellow precipitate that formed was filtered and washed with cooled ethanol to give 11a as a pale yellow powder (4.22 g, 20% yield), m.p. 132-133° C.

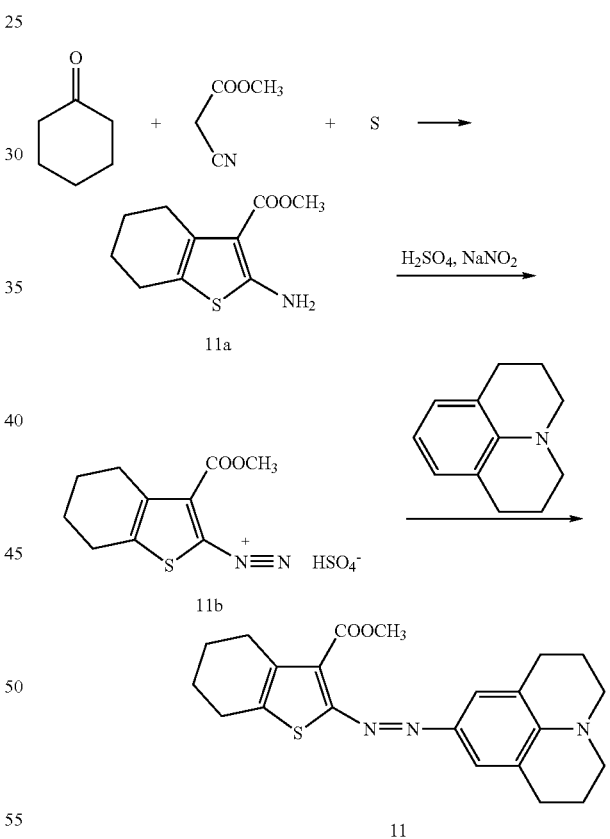

The 2-aminothiophene derivative 11a (2.96.0 g, 0.014 mol) was dissolved in a minimum amount of dimethylformamide (10 ml), and sulfuric acid (8 ml, 54% V/V) was added. The mixture was cooled to 0-5° C. with stirring for half an hour. Sodium nitrite (0.97 g, 0.014 mol) was dissolved in water (10 ml) and cooled to 0-5° C. to form dilute nitrous acid. This solution was slowly added to the 2-aminothiophene derivative solution, with the temperature being kept in the range of 0-5° C. Stirring was continued for one hour, after which the diazonium salt 11b was formed.

Julolidine (2.50 gm, 0.014 mol) was dissolved in a solution prepared from water (10 ml) and hydrochloric acid (5 ml, 10M), and the solution was cooled to a temperature between 0-5° C. The diazonium solution 11b was added to the julolidine coupling component solution slowly over a period of one hour to keep the temperature below 5° C. The reaction mixture was stirred for 2 hours, during which the temperature was raised to room temperature. The pH of the solution was raised by adding sodium hydroxide solution (5-10%) to obtain a pH in the range between 5.5 and 7. The precipitated dye 11 was filtered and washed with plenty of water to get rid of the excess sodium hydroxide, then recrystallized from an ethyl acetate/petroleum ether (40-60) mixture (8:2), m.p. 98-103° C., (68% yield).

Example 12

The reaction scheme for the synthesis of azo dye 12 is shown below. In a Gewald reaction, diethylamine (8 ml) was added to a solution of equimolar quantities of cycloheptanone (11.2 g, 0.10 mol) and malononitrile (6.60 g, 0.10 mol) in ethanol, and the mixture was refluxed for 10 minutes. Then sulfur (3.53 g, 0.11 mol) was added, and the solution was refluxed for a further 3 hours. The pale yellow precipitate formed was filtered and washed with cooled ethanol to give 12a as a pale yellow powder (6.72 g, 35% yield), m.p. 121-123° C.

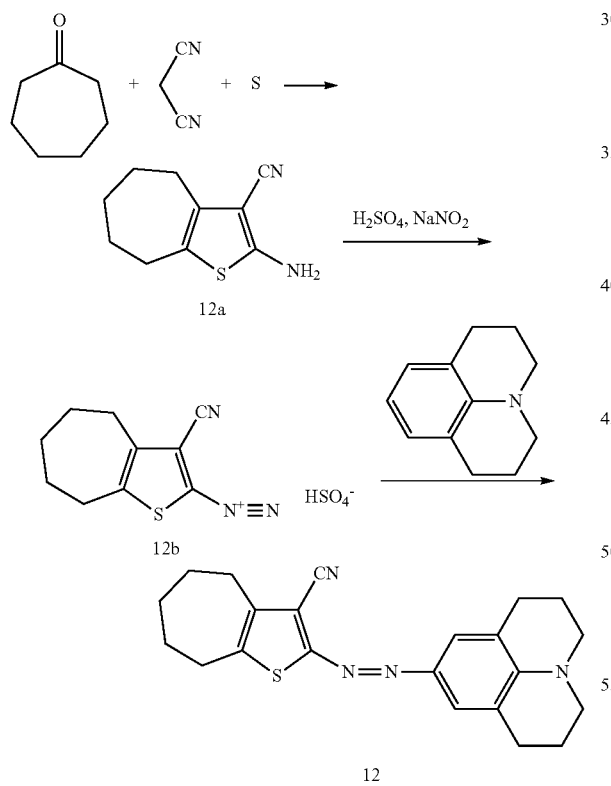

The 2-aminothiophene derivative 12a (5.0 g, 0.026 mol) was dissolved in a minimum amount of dimethylformamide (10 ml), and sulfuric acid (8 ml, 54% V/V) was added. The mixture was cooled to 0-5° C. with stirring for half an hour. Sodium nitrite (1.79 g, 0.026 mol) was dissolved in water (10 ml) and cooled to 0-5° C. to form dilute nitrous acid. This solution was slowly added to the 2-aminothiophene derivative solution, with the temperature being kept in the range of 0-5° C. Stirring was continued for one hour, after which the diazonium salt 12b was formed.

Julolidine (4.63 g, 0.026 mol) was dissolved in a solution prepared from water (10 ml) and hydrochloric acid (5 ml, 10M), and the solution was cooled to a the temperature between 0-5° C. The diazonium solution 12b was added to the julolidine coupling component solution slowly over a period of one hour to keep the temperature below 5° C. The reaction mixture was stirred for 2 hours, during which the temperature was raised to room temperature. The pH of the solution was raised by adding sodium hydroxide solution (5-10%) to obtain a pH in the range between 5.5 and 7. The precipitated dye 12 was filtered and washed with plenty of water to get rid of the excess sodium hydroxide, then recrystallized from an ethyl acetate/petroleum ether (40-60) mixture (8:2), m.p. 184-186° C., (76% yield).

Example 13

The reaction scheme for the synthesis of azo dye 13 is shown below. In a Gewald reaction, diethylamine (8 ml) was added to a solution of equimolar quantities of cycloheptanone (11.2 g, 0.10 mol) and methyl cyanoacetate (9.90 g, 0.10 mol) in ethanol, and the mixture was refluxed for 10 minutes. Then sulfur (3.53 g, 0.11 mol) was added, and the solution was refluxed for a further 3 hours. The pale yellow precipitate that formed was filtered and washed with cooled ethanol to give 13a as a pale yellow powder (6.53 g, 29% yield), m.p. 97-98° C.

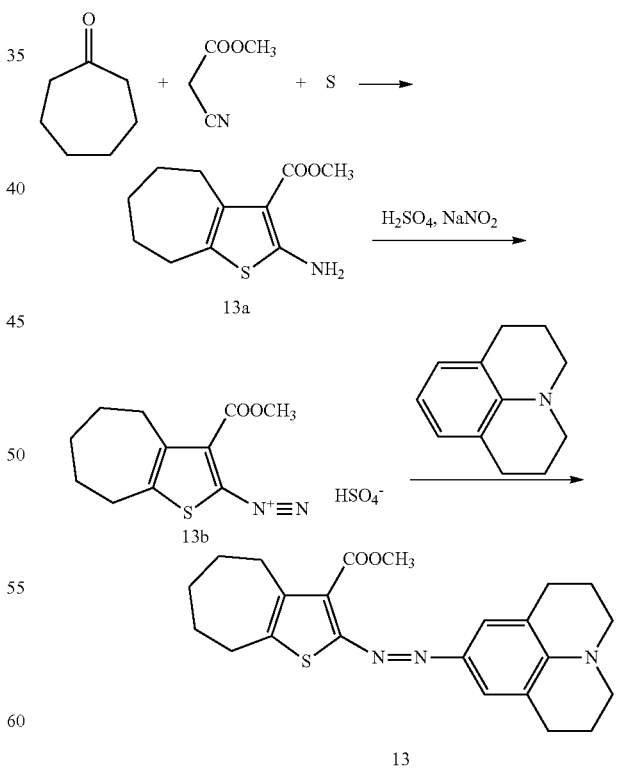

The 2-aminothiophene derivative 13a (2.93 g, 0.013 mol) was dissolved in a minimum amount of dimethylformamide (10 ml), and sulfuric acid (8 ml, 54% V/V) was added. The mixture was cooled to 0-5° C. with stirring for half an hour.

Sodium nitrite (0.90 g, 0.013 mol) was dissolved in water (10 ml) and cooled to 0-5° C. to form dilute nitrous acid. This solution was slowly added to the 2-aminothiophene derivative solution, with the temperature being kept in the range of 0-5° C. Stirring was continued for one hour, after which the diazonium salt 13b was formed.

Julolidine (2.25 g, 0.013 mol) was dissolved in a solution prepared from water (10 ml) and hydrochloric acid (5 ml, 10M), and the solution was cooled to the temperature between 0-5° C. The diazonium solution 13b was added to the julolidine coupling component solution slowly over a period of one hour to keep the temperature below 5° C. The reaction mixture was stirred for 2 hours, during which the temperature was raised to room temperature. The pH of the solution was raised by adding sodium hydroxide solution (5-10%) to obtain a pH in the range between 5.5 and 7. The precipitated dye 13 was filtered and washed with plenty of water to get rid of the excess sodium hydroxide, then recrystallized from an ethyl acetate/petroleum ether (40-60) mixture (8:2), m.p. 149-153° C., (25% yield).

The azo dyes 1 through 13 can be used to color polyesters, polyethylene, and other plastics. The dyes have a high molar absorption in polymers and exhibit a deep hue of color on polyester. The colors produced by azo dyes 1 through 13 and their UV absorption peaks in dimethylformamide (DMF) solvent are shown in Table 1.

TABLE I

UV Absorption Peak and Color

| Dye No. | Wavelength(nm) | Color |
|---|---|---|
| 1 | 558 | Blue |
| 2 | 574 | Blue |
| 3 | 595 | Deep Blue |
| 4 | 572 | Blue |
| 5 | 568 | Blue |
| 6 | 575 | Blue |
| 7 | 570 | Blue |
| 8 | 573 | Blue |
| 9 | 569 | Blue |
| 10 | 562 | Blue |
| 11 | 630 | Deep Blue |
| 12 | 560 | Blue |
| 13 | 556 | Blue |

In use, the dyes may be applied to a substrate in any conventional manner. For example, in the case of polyester, two parts (by weight) of the azo dye in finely ground form may be mixed with ninety-eight parts of polyester in the form of chips, and the resulting mixture is then melted and spun into filaments in conventional melt-spinning equipment. Alternatively, a paste may be prepared by grinding a mixture of one part (by weight) of the azo dye to two parts of a dispersing agent, such as Dodamol. The paste is added to ninety-seven parts water with rapid stirring to obtain an aqueous dispersion of the dye. The pH of the dispersion is adjusted to 4.5-5.0 by adding 1% acetic acid. The polyester is then dyed with the dispersion at 100° C.

It is to be understood that the present invention is not limited to the embodiments described above, but encompasses any and all embodiments within the scope of the following claims.

I claim:

1. An azo dye of the formula:

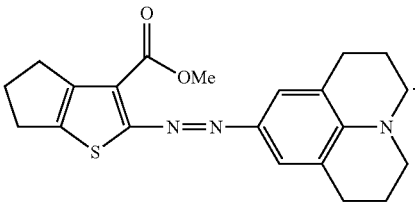

9

2. An azo dye of the formula:

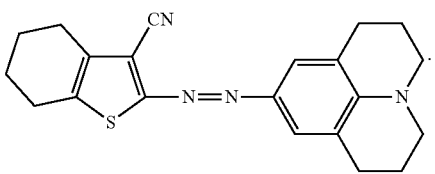

10

3. An azo dye of the formula:

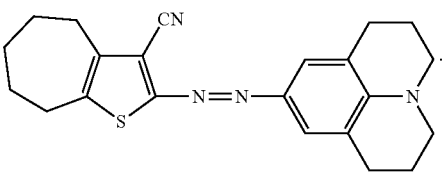

12

4. An azo dye of the formula:

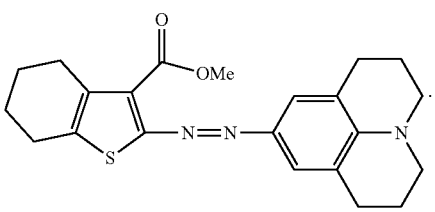

11

5. An azo dye of the formula:

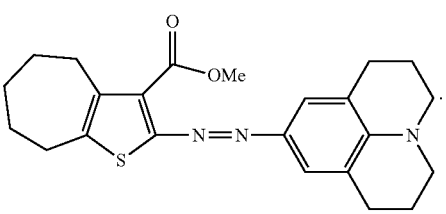

13

* * * * *